(12) United States Patent
Baumgardner et al.

(10) Patent No.: US 7,147,654 B2
(45) Date of Patent: Dec. 12, 2006

(54) TREATMENT SITE COOLING SYSTEM OF SKIN DISORDERS

(75) Inventors: Jonathan M. Baumgardner, Roseville, CA (US); David R. Hennings, Roseville, CA (US); Thomas F. Johnston, Jr., Roseville, CA (US); B. Eric Taylor, Roseville, CA (US); Mitchell P. Goldman, Roseville, CA (US)

(73) Assignee: Laserscope, San Jose, CA (US)

( * ) Notice: Subject to any disclaimer, the term of this patent is extended or adjusted under 35 U.S.C. 154(b) by 0 days.

(21) Appl. No.: 10/351,273

(22) Filed: Jan. 24, 2003

(65) Prior Publication Data
US 2004/0147986 A1 Jul. 29, 2004

(51) Int. Cl.
*A61N 5/06* (2006.01)
*A61B 18/18* (2006.01)

(52) U.S. Cl. .............................. 607/88; 606/13; 606/9

(58) Field of Classification Search .................. 607/94, 607/88, 90, 100, 104, 89; 606/2, 3, 9–18, 606/33
See application file for complete search history.

(56) References Cited

U.S. PATENT DOCUMENTS

| | | | |
|---|---|---|---|
| 3,693,623 A * | 9/1972 | Harte et al. ..................... 606/9 |
| 5,344,418 A | 9/1994 | Ghaffari |
| 5,405,368 A * | 4/1995 | Eckhouse .................... 607/88 |
| 5,662,644 A * | 9/1997 | Swor ........................... 606/9 |
| 5,720,772 A * | 2/1998 | Eckhouse .................... 607/88 |
| 5,789,755 A | 8/1998 | Bender |
| 5,814,040 A * | 9/1998 | Nelson et al. ................. 606/9 |
| 5,820,626 A | 10/1998 | Baumgardner |
| 5,836,999 A * | 11/1998 | Eckhouse et al. ............. 607/88 |
| 5,885,274 A | 3/1999 | Fullmer et al. |
| 5,968,034 A | 10/1999 | Fullmer et al. |
| 5,976,123 A | 11/1999 | Baumgardner et al. |
| 6,028,316 A * | 2/2000 | Bender ..................... 250/492.1 |
| RE36,634 E | 3/2000 | Ghaffari |
| 6,080,147 A * | 6/2000 | Tobinick ........................ 606/9 |
| 6,117,335 A | 9/2000 | Bender |
| 6,171,301 B1 * | 1/2001 | Nelson et al. ................. 606/9 |
| 6,200,308 B1 * | 3/2001 | Pope et al. .................... 606/9 |
| 6,200,466 B1 | 3/2001 | Bender |
| 6,214,034 B1 * | 4/2001 | Azar ........................... 607/89 |
| 6,413,253 B1 | 7/2002 | Koop et al. |
| 6,451,007 B1 | 9/2002 | Koop et al. |
| 2002/0173780 A1 * | 11/2002 | Altshuler et al. .............. 606/9 |
| 2002/0183811 A1 * | 12/2002 | Irwin .......................... 607/94 |
| 2003/0004501 A1 * | 1/2003 | Wilkens et al. ............... 606/9 |
| 2004/0034397 A1 * | 2/2004 | Lin ............................ 607/94 |

OTHER PUBLICATIONS

U.S. Appl. No. 60/422,566, filed Oct. 3, 2002.
U.S. Appl. No. 09/805,568, filed Mar. 12, 2001.
U.S. Appl. No. 10/007,310, filed Sep. 12, 2000.

(Continued)

*Primary Examiner*—Michael Peffley
(74) *Attorney, Agent, or Firm*—Mark A. Haynes; Haynes Beffel & Wolfeld LLP

(57) ABSTRACT

A method and apparatus for treating skin disorders includes a source of pulsed near black body electromagnetic energy and a means of delivering this energy to a treatment site. A means for cooling the treatment site is described. The number of pulses and intensity of the energy can be varied. Optical filters are used to limit the spectrum of energy emitted and the filters are cooled to allow high-energy operation. The size of the treatment spot is controlled by a series of apertures.

20 Claims, 14 Drawing Sheets

OTHER PUBLICATIONS

U.S. Appl. No. 10/160,519, filed May 31, 2002.
U.S. Appl. No. 09/934,356, filed Aug. 21, 2001.
U.S. Appl. No. 09/135,330, filed Jul.18, 1998.
J. A. Parrish et. al., Journal of Investigative Dermatology, v. 76 (1981) pp. 359-362, "Action Spectrum for the Phototherapy of Psoriasis".

PCT Written Opionion of the International Searching Authority, Jan. 21, 2005.

PCT International Search Report of Application No. PCT/US2004/002256, Jan. 21, 2005.

* cited by examiner

Wavelength (nm)

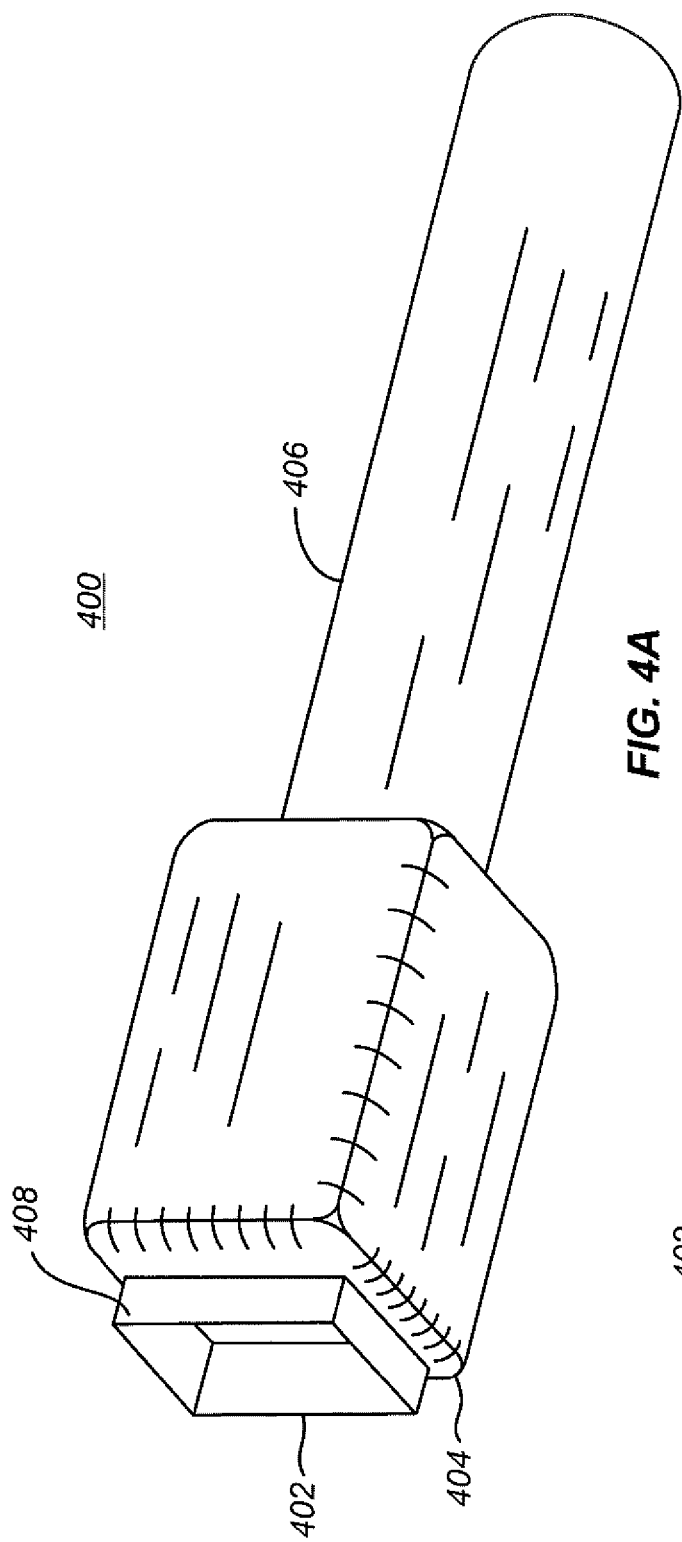
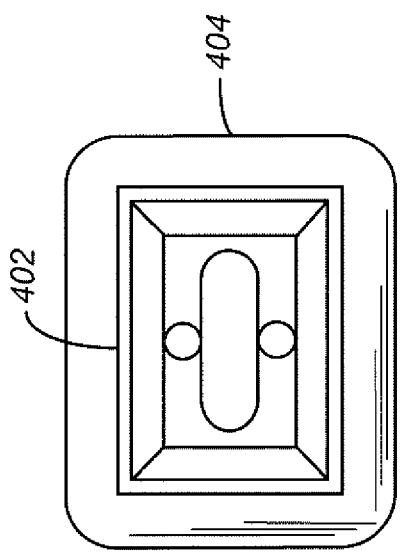

*Straight Lamp*

Treatment Site

Water Cooled Filter

TREATMENT SITE COOLING SYSTEM OF SKIN DISORDERS

FIELD OF THE INVENTION

The present invention is related to therapeutic applications for light energy, and in particular, to controlled, high-power flashlamps for delivery of near black body electromagnetic radiation.

BACKGROUND OF THE INVENTION

Approximately 3% of the United States population have been diagnosed with inflammatory skin disease such as psoriasis. There are two main treatment modalities. One is treatment with drugs and the other is treatment with light, typically UVA or UVB.

The problems with the drug treatments are the potential side effects. Steroids can cause thinning of the skin, bruising and stretch marks. Systemic drugs can cause high blood pressure, birth defects and damage kidneys.

The light based treatment is effective without the side effects but requires 15 to 30 treatments to be effective. These are typically done in a "tanning booth" device, which exposes healthy skin as well as affected skin to the treatment. Thus the dosage is limited to one to two MED's (minimal erythemal dose) to avoid sunburning and blistering of healthy skin. This requires the patient to return every few days, for a total of 15 to 30 treatments to reach a cumulative therapeutic dose.

A device is needed that will provide the benefits of the light treatments in a more efficient manner. The proposed device will provide large amounts of energy directly to the affected site in a short amount of time. As affected skin tolerates doses at one sitting of three or more times the MED of healthy skin, this reduces the number of treatment sessions required to reach the therapeutic dose. This method also eliminates the need to expose healthy skin to the treatment.

Prior art systems using flashlamps have not been capable of significant light output in the UV or IR regions. The reason for this is in the design of the flashlamp and the power supply that drives the lamp. Conventional flashlamp systems are capable of producing therapeutic output primarily in the visible region (500 nm to 650 nm) and in the near IR (650–850 nm). In contrast, the present invention allows and uses therapeutic outputs in the UV as well as the mid IR (850 nm-1300 nm).

SUMMARY OF THE PRESENT INVENTION

The present invention includes devices for the effective treatment of skin disorders such as psoriasis. The device will be capable of delivering single pulses or bursts containing several pulses. Each of these pulses may reach energies from between about 1 to about 50 J/pulse. This device will operate as a near black body radiator.

The device may have an energy output per pulse of between about 0.2–10 J in the range of between about 320 nm to 400 nm (UVA) and an energy output of between about 0.1–2 J in the range of between about 290 nm-320 nm (UVB).

In a preferred embodiment, there will be a delivery system consisting of a flashlamp, a reflector to direct the energy onto the treatment site and filters to control the output spectrum.

In another preferred embodiment, both the filters and flashlamp are water-cooled. Cooling the filters with flowing water allows higher energies to be delivered through the filters without damaging them.

In another embodiment, the flashlamp and filters will be cooled by flowing air.

The burst energy is adjustable by adding or dropping the number of pulses in the burst (typically one to six). The total output energy is adjustable from between about 1 J to about 180 Joules.

By operating the flashlamp plasma, or discharge, at a very high temperature, it is possible to achieve near black body operation. This means that it is possible to operate the device so that the energy produced is enhanced in the desired portion of the spectrum.

It will be understood by those skilled in the art that the peak energy developed by other devices is centered in the visible portion of the spectrum. This means that when filters are employed to allow operation in UVA or UVB, they are actually filtering out most of the output energy. The present invention centers the peak energy at about 330 nm. This allows more energy to be delivered in the desired wavelength range reducing the required number treatment sessions.

In another embodiment the present invention will provide a cooling spray to the treatment site to protect the skin and provide an analgesic effect. This spray can be carbon dioxide gas, cryogen, air/water or other cooling agents.

A handpiece for treatment of skin conditions comprises a housing having a handle portion and a front end adjacent to the handle portion, the front end having a light transmissive opening; a flashlamp disposed in the housing for generating an output electromagnetic radiation through the opening onto a treatment site; and a treatment site cooling system including a port disposed on the housing near the opening, adapted for delivery of a cryogenic cooling fluid to protect skin in the treatment site from burning caused by exposure to the electromagnetic radiation.

In a preferred embodiment, the device is used for vascular disorders, hair stimulation and removal, acne removal, scar removal and tattoo removal. Spot sizes generated are up to 16×46 mm or more or less. The utilities required include 110 Volts AC to 240 Volts AC or more or less, and a source of cooling fluid for the flashlamp and a source of cooling agent for the treatment area. The system is pulsed with a width of about 25–500 milliseconds, or more preferably about 10–100 milliseconds or more or less. Cryogen or other cooling spray duration is about 200–400 msec. The wavelength varies with the application or handpiece model, and is typically between about 300–1200 nm or more or less. The handpiece can be a direct delivery handpiece and cooling can be achieved using a sapphire contact. Fluence of energy is between about 4–40 $J/cm^2$ or more or less. Treatment speeds are up to about 7–8 $cm^2/sec$ or more or less. The handpiece can operate at a rate of about 1 Hz or more or less.

Possible filters which can be used in the present invention are typically related to the specific, intended application: vascular treatment utilizes wavelengths between about 560–1200 nm or more or less (OG 550); acne treatment utilizes wavelengths between about 405–420 nm or more or less (FGG, BG 26, BG 14, optionally solarized); hair treatment utilizes wavelengths between about 640–1200 nm or more or less (RG 630); and other photo rejuvenation processes utilizes wavelengths between about 800–3000 nm.

BRIEF DESCRIPTION OF THE DRAWINGS

The invention is illustrated below and represented schematically in the following drawings:

FIG. 4A is a representative isometric view of a preferred embodiment of the handpiece of the present invention for treating skin disorders according to the method of the present invention.

FIG. 4B is a representative view of the treatment window in the front end of the handpiece shown in FIG. 4A.

DETAILED DESCRIPTION OF THE PREFERRED EMBODIMENT

Figure 1A:
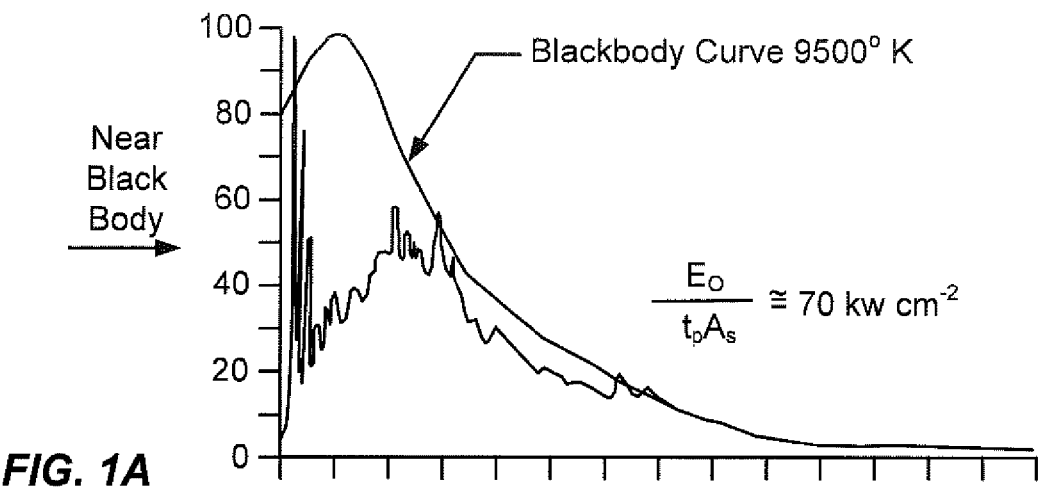
FIGS. 1A–1C show the spectra of a xenon-filled flashlamp pulsed at various current densities reaching into the blackbody regime at which the apparatus of the present invention operates.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

Description of Near Black Body Operation

The present invention is assigned to the same assignee as the Bender patents (U.S. Pat. No. 6,117,335 and No. 6,200,466) disclosing a flashlamp system operating in the near black body regime to generate UV light for the purpose of decontaminating water. The relevant discussion of the physics of flashlamps contained therein is incorporated here by reference.

1) Flashlamp Spectra.

A continuum mode of radiation is created by strongly ionizing the gas within the flashlamp. This continuum radiation approaches a high-emissivity blackbody radiation profile with increasing flashlamp power density. Illustrated in FIG. 1 are spectra for a xenon-filled flashlamp at three different levels of power density (see ILC Technology, Inc., Technical Bulletin No. 2, FIG. VIII). Power density is defined as:

$$P_0 = (E_0/t_p A_s) \text{ (watt/cm}^2) \tag{1}$$

where: $E_0$=lamp discharge energy (joules);
$t_p$=pulse duration FWHM (seconds); and
$A_s$=lamp bore surface area (cm$^2$).

Figure 1B:
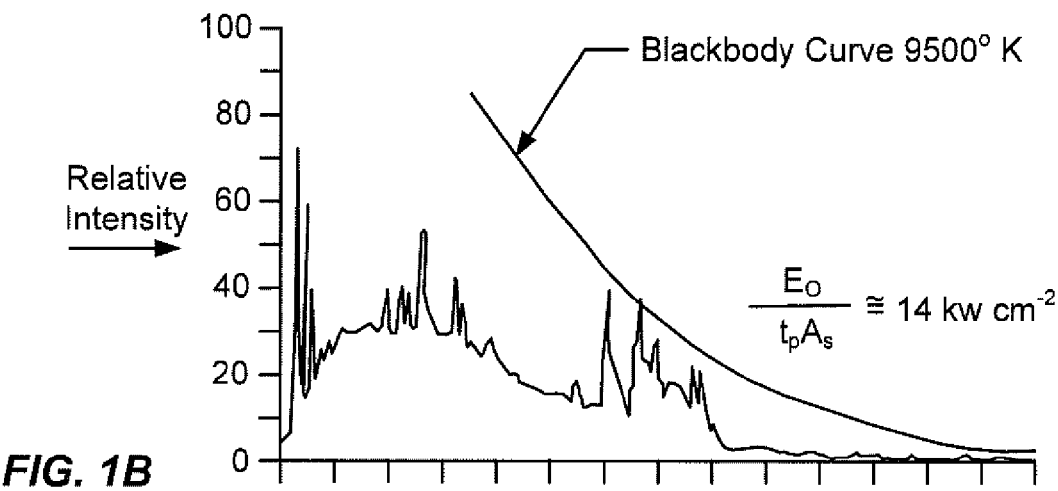
Figure 1C:
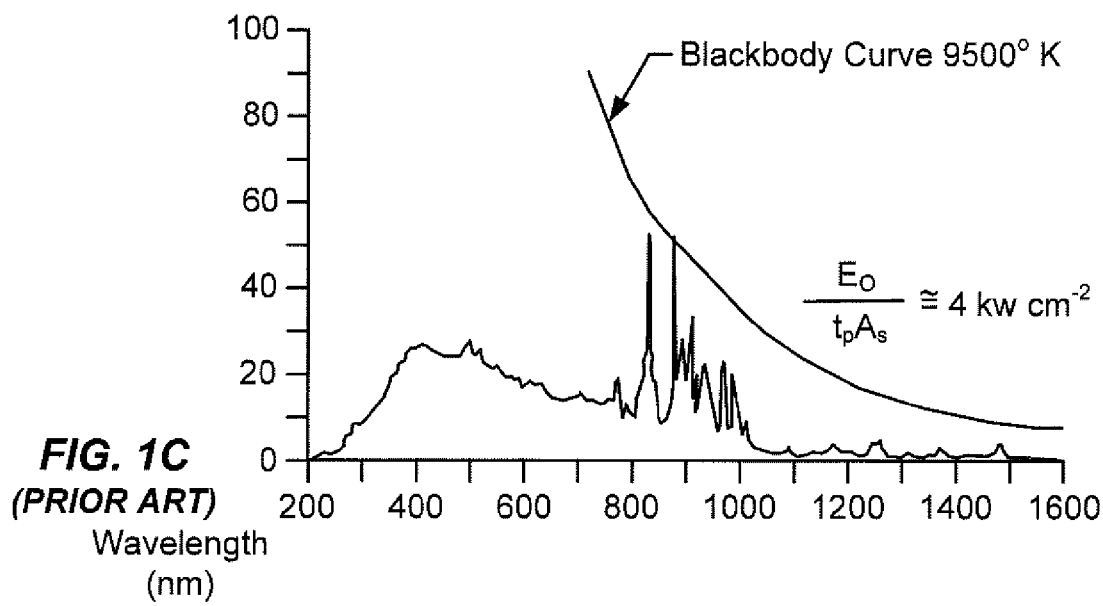

In FIG. 1C, at the lowest power density of about 4 kW/cm$^2$, it is evident that the emission contains sharp peaks (line spectra) superposed on a low continuous background. Line spectra are the result of the electrons in the discharge current colliding with atoms or ions, causing within them internal transitions between bound energy levels. In relaxing from these excited states, the atoms or ions emit light energy at discrete wavelengths (bound-bound transitions), or line spectra. As the power density is increased in FIG. 1B to 14 kW/cm², the proportion of continuous background increases. The continuous spectrum is generated by the deceleration of electrons in collisions with ions (Bremstrahlung) and by collisions that ionize (bound-free transitions), both of which occur more frequently at higher power densities. At the highest power density of about 70 kW/cm² in FIG. 1A, the envelope of the continuum spectra approachs the reference curve, which is superposed to show the spectral distribution of an ideal black body radiator at 9500° K absolute temperature. The peak of the continuous spectrum also lies in the UV (at a wavelength less than 400 nm) and the continuous spectrum fully dominates the line spectra. These are the charactersitics of the "near black-body" state, where the photons, and charged and neutral particles of the discharge plasma near thermal equilibrium. The approach is gradual with increasing power density; there is no abrupt demarcation point. However, conventional rules of thumb for operation of a flashlamp as a near black-body radiator are that the power density exceeds 25 kW/cm², or that the plasma temperature reaches 9500° K.

2) Flashlamp Lifetime

The flashlamp must be optimized to deliver the maximum amount of useful energy with good conversion efficiency while still maintainging a useful long lifetime. Driving the lamp harder, while producing more UV, shortens the lamp life considerably. This tradeoff must be balanced by careful consideration of pulse duration and energy input.

To maintain reasonable lamp life, the input energy to the flashlamp must be kept below 18% of the theoretical single-shot explosion energy limit. Various models are used to predict lamp life. For a lamp that is driven hard, the expected failure mode is the limit imposed by envelope material tensile stress, seal strength, and wall abalation and cracking. Then the following formulas show how the explosion energy is related to the lamp geometry, envelope material, input energy, and pulse duration (see ILC Tech. Bulletin 2).

From the dimensions and envelope material of the flashlamp, an explosion-energy constant ($K_e$) is obtained:

$$K_e = f(d) l d \tag{2}$$

where:
- f(d)=silica power function based on material transparency, thermal conductivity, wall thickness, and bore diameter, W sec$^{1/2}$ cm$^{-2}$,
- l=discharge length of the flashlamp, cm,
- d=bore diameter of the flashlamp, cm.

The single-shot explosion energy $E_x$ then is:

$$E_x = K_e (t_p/2)^{1/2}. \tag{3}$$

The lamp lifetime LT, in number of shots, is approximated by:

$$LT = [E_o/E_x]^{-b} \tag{4}$$

where the flashlamp input energy $E_o$ is in Joules, and the constant b depends on bore diameter and wall thickness. For the small bore lamps of 6 mm diameter or less (appropriate for mounting in a handheld device for dermatologic treatments) the constants to be used in Eq. (4) are $K_e$=24600, and b=8.5. To be conservative in the case of a lamp used in a commercial product, the number of shots predicted by Eq. (4) is frequently reduced by some safety factor such as $10^{-3}$.

3) Advantages of a Near Blackbody Source in the Treatment of Skin Disorders

An ideal black-body emitter of a given temperature emits more energy than any real source with the same surface temperature. A flashlamp driven to near-blackbody operation thus approaches theoretical limits, and is a high power emitter providing light energy over broad spectrum. This makes possible treatments with a single source for a wide range of skin disorders. In the phototherapy treatment of skin disease, various wavelength bands are used:

| Skin Condition | Wavelengths of Treatment |
|---|---|
| psoriasis | 297–320 nm |
| vitiligo | 297–320 nm |
| acne | 405–420 nm |
| hair removal | 640–1200 nm |
| reduction of vascularization | 450–600 nm |
| roseacea | 450–600 nm |

The continuous nature of near blackbody radiation allows any of these wavelengths to be made available by spectral filtering in the delivery system, to pass the desired wavelengths, and reject the unwanted bands. Additionally, the peak wavelength of the blackbody spectral distribution can be tuned (by the control of the ratio $E_o/t_p A_s$ as in FIG. 1) to weight the spectrum of the lamp for more output in the desired bands to make the lamp more efficient for a given application. Finally, the established nature of the life limits in this mode of operation permits a rational tradeoff to be made between lamp emittance (also called radiant exitance), spectral distribution, and lifetime.

4) Adjusting the Near-Blackbody Spectrum

Figure 2:
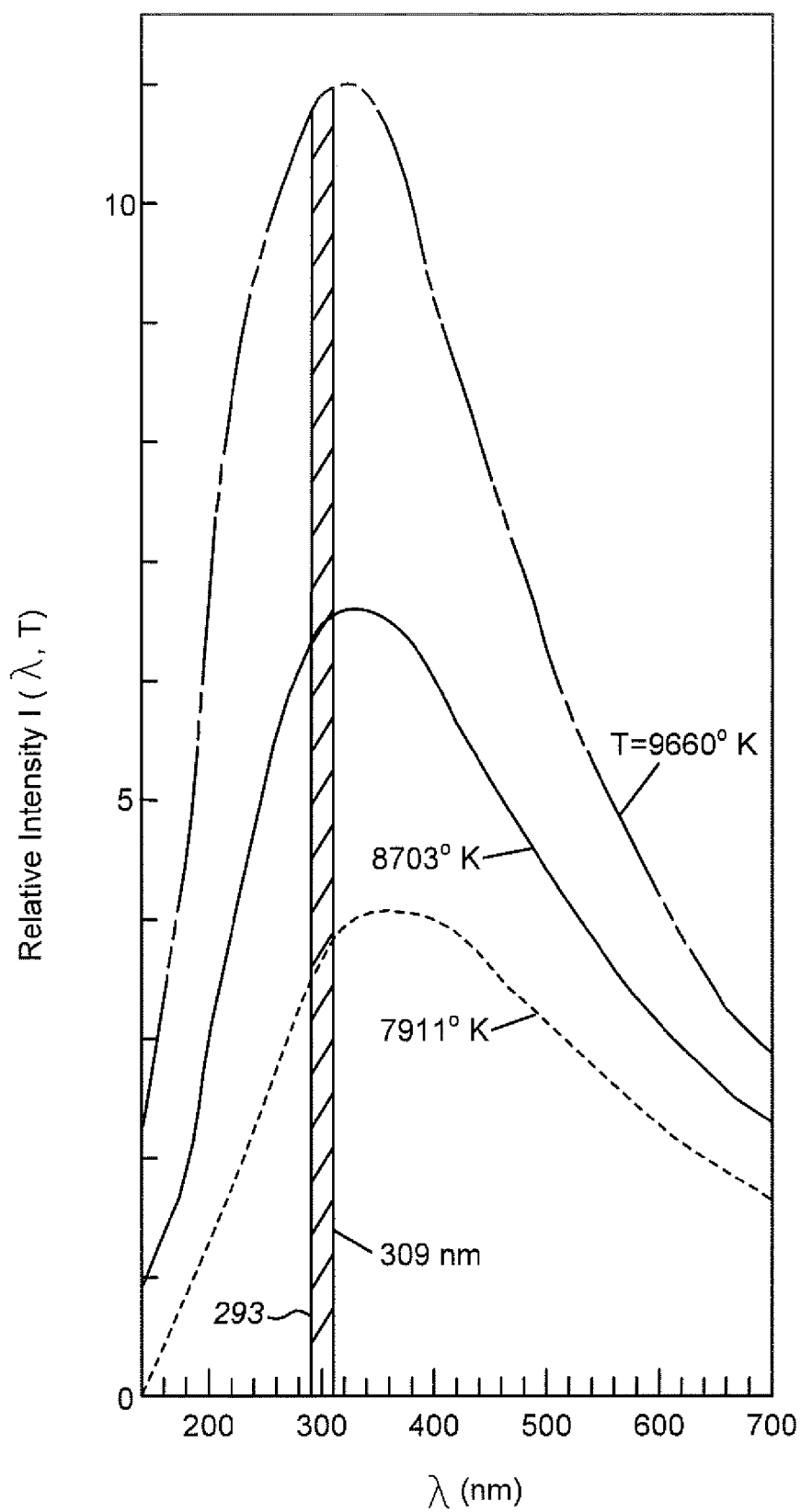
FIG. 2 shows three blackbody spectral distribution curves in the range of operation of the present invention, with the prefered wavelengths for the phototherapy treatment of psoriasis shaded. This is used in a discussion of selecting an optimum lamp operating point in a dermatological application.

The wavelength of the peak of the blackbody spectral distribution shifts with the surface temperature T of the emitter according to Wein's Displacement Law:

$$l_{peak} = 2898/T \tag{5}$$

where $l_{peak}$ is in micrometers, and T is the absolute temperature, in Kelvins. FIG. 2 shows this peak wavelength shift for three different blackbody temperatures in the range of operation of the device of the present invention. The wavelength of the peak of the curve moves from 366 nm for the lowest curve at temperature of 7911° K, to 333 nm for the middle curve at 8703° K, and to 300 nm for the upper one at 9660° K.

For the change from the lowest to the highest temperature of FIG. 2, the maximum emittance per unit wavelength interval (relative intensity) rises by a factor of 2.7, in accordance with Plank's Radiation Formula (see Bender's patent, U.S. Pat. No. 6,117,335, Eq. (2)). When this formula is integrated over all emitting wavelengths, the Stefan-Boltzmann Law results, which states that the total power emitted over all wavelengths, per cm² of blackbody surface area, increases with the fourth power of the surface's absolute temperture:

$$P = {_s}T^4. \tag{6}$$

The proportionality constant is called Stefan's constant and is equal to:

$$_s = 5.67 \times 10^{-12} W\, cm^{-2} (° K)^{-4}.$$

The power emitted from the flashlamp can be estimated as the input energy $E_o$ times the average radiation efficiency (0.85) to get the total radiation, divided by the average time over which this energy is delivered (the pulse length $t_p$). Balancing this power against the that from the Stefan-Boltzmann law gives the equivalent blackbody temperature of the lamp, $T_{BB}$, the temperature of a perfect blackbody emitting over the same area as the lamp at the same total power:

$$A_s T_{BB}^4 = (\text{Total Power}) = (0.85)(E_o/t_p)$$

or $$T_{BB} = [(0.85)(E_o/t_p A_s)]^{1/4}. \qquad (7)$$

The temperature given by Eq. (7) is an upper bound for the plasma temperature of the lamp, since to the degree that a portion of the output spectrum may still exist as line spectra, there is less power to be dissipated as blackbody radiation and a slightly lower plasma temperature may result.

Eq.(7) shows directly why the lamp spectrum moves towards the continuous blackbody spectrum as the lamp power density $E_o/t_p A_s$ of Eq. (1) and FIG. (1) is increased to balance the increasing power density, the average energy (temperature) of the particles in the plasma must increase to radiate more, and the thermal interactions swamp the competing means of radiating.

In general, to achieve a higher plasma temperature to increase the energy radiated into a desired bandwidth, or to increase the overall output energy, the application of shorter pulses of electrical input energy will be useful. Flashlamps are often driven with pulse forming networks (PFN's) where the input energy is determined by the charge on the capacitance C, and the time to deliver charge to the lamp is determined by the inductance L. Varying L conveniently adjusts the power density delivered and thus the lamp's blackbody radiation characteristics.

The tradeoff is that the lamp life decreases with explosion energy $E_x$, which by Eq.(3) is also a function of the pulse length $t_p$. Substituting Eq.(3) into Eq.(4) shows that the expected lifetime LT of the lamp scales proportionally to:

$$LT = \text{constant } (t_p)^{4.25}, \qquad (8)$$

a rapid decrease as the pulse length decreases.

5) Optimizing TBB for Dermatological Applications

In the Bender patents there is presented the logic for optimizing the operating point of the flashlamp for his application of water decontamination through control of the pulse length. In dermatological applications, the situation is analogous.

For purposes of concreteness or to be more definite, consider the most demanding dermatological application, that of the phototherapy treatment to clear psoriasis, which requires application of ultraviolet light in the range of 297–320 nm. Actually, the most effective ultraviolet band is 293 nm to 309 nm band (see J. A. Parrish et. al., *Journal of Investigative Dermatology*, v. 76 (1981) pp. 359–362, "Action Spectrum for the Phototherapy of Psoriasis"). These wavelengths are the points on the action spectrum where the effectiveness in clearing placque drops to 10% of that at the 300 nm peak of the spectrum. These limits are shown shaded in FIG. 2. However, wavelengths shorter than 297 nm lie within what is believed to be the photocarcinogenesis action spectrum for humans (though it was measured on hairless mice; see C. A. Cole, et. al., *Photochemistry and Photobiology*, v. 43 (1986) pp. 275–284, "An Action Spectrum for UV Photocarcinogenesis"). Thus the repeated exposure to significant energy at wavelengths shorter than this will eventually cause skin cancer. Psoriasis sufferers generally accept this small risk, where the spectra overlap, to be cleared of the effects of their disease.

Thus both applications have a short wavelength limit, below which the lamp output is not useful. In Bender's case, this was the transparency limit of the lamp envelope, about 185 nm. In the case of psoriasis treatment, the lower limit is the turn-on of the carcinogenesis spectrum at 297 nm. Bender's logic is to adjust the pulse length, to shift the peak wavelength of the blackbody spectral distribution just to the long-wavelength side of the useful short wavelength limit. He showed that in generating light in the useful band for the water decontamination application (which extended from 185 nm up to 400 nm) that the efficiency did not depend strongly on $T_{BB}$ as long as the blackbody peak wavelength, and the useful short wavelength limit were close. Essentially, driving the lamp harder at this point, to move the spectrum down to shorter wavelengths, generated more light that fell in wavelength below the short wavelength limit, with a severe penalty in lamp lifetime. Bender's logic determines an optimum operating point—position the blackbody spectral peak just to the right of the short wavelength limit at the first acceptable value for lamp lifetime. For the psoriasis application, the same logic gives the middle curve of FIG. (2).

Actually, in the psoriasis application the optimum blackbody peak moves further to the right when it is considered that it is often an advantage to use a greater number of lower energy shots, to give adequate resolution in doseage control by counting the number of shots. The lamp life considerations favor this approach.

For example, five shots to complete a dose gives a 20% doseage control with ±1 shot added or dropped. This is about what is desired. Consider then the alternatives of the two operating points represented by the two lower curves of FIG. 2. From the Stefan-Boltzmann law (Eq. (6)), the power densities for the two lower curves are in the ratio of 1:1.46. Holding the input energy to the lamp constant, reaching these two operating points would then require pulse lengths in the ratio of 1:1/1.46. By the scaling law Eq.(8), the shorter pulse length would reduce the lamp lifetime by a factor of $1/5.06 = 0.2 = [1/1.46]^{4.25}$. The useful energy per shot with the shorter pulse length is only 46% larger, or the total dose with the lower curve can be reached in 7 shots, if it were reached in 5 shots with the middle curve as operating point. Using 46% more shots, with 5 times as many shots available from the lamp, is a better tradeoff if the resultant treatment times are acceptable to the doctor and patient.

FIGS. 1A–1C show the spectra of a xenon bore flashlamp pulsed at various power densities reaching into the near blackbody regime at which the apparatus of the present invention operates.

Apparatus and Method of Use

FIG. 4A is a representative isometric view of a preferred embodiment of the handpiece 400 of the present invention for treating skin disorders according to the method of the present invention. FIG. 4B is a representative view of the treatment window 402 in the front end 404 of the handpiece 400 shown in FIG. 4A. The handpiece 400 comprises an elongated handle portion 406 coupled to the front end 404 that has a hood 408 which protrudes outwardly from a flashlamp in defining a treatment site.

Figure 5A:
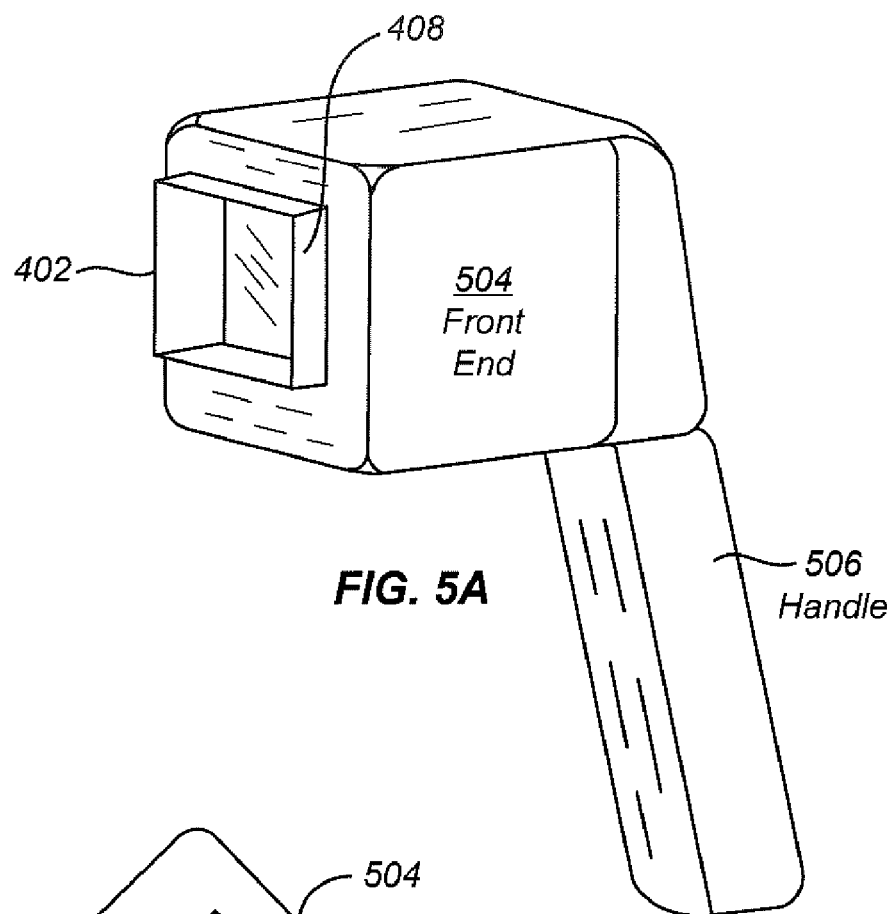
FIG. 5A is a representative isometric view of another preferred embodiment of the handpiece of the present invention for treating skin disorders according to the method of the present invention.
Figure 5B:
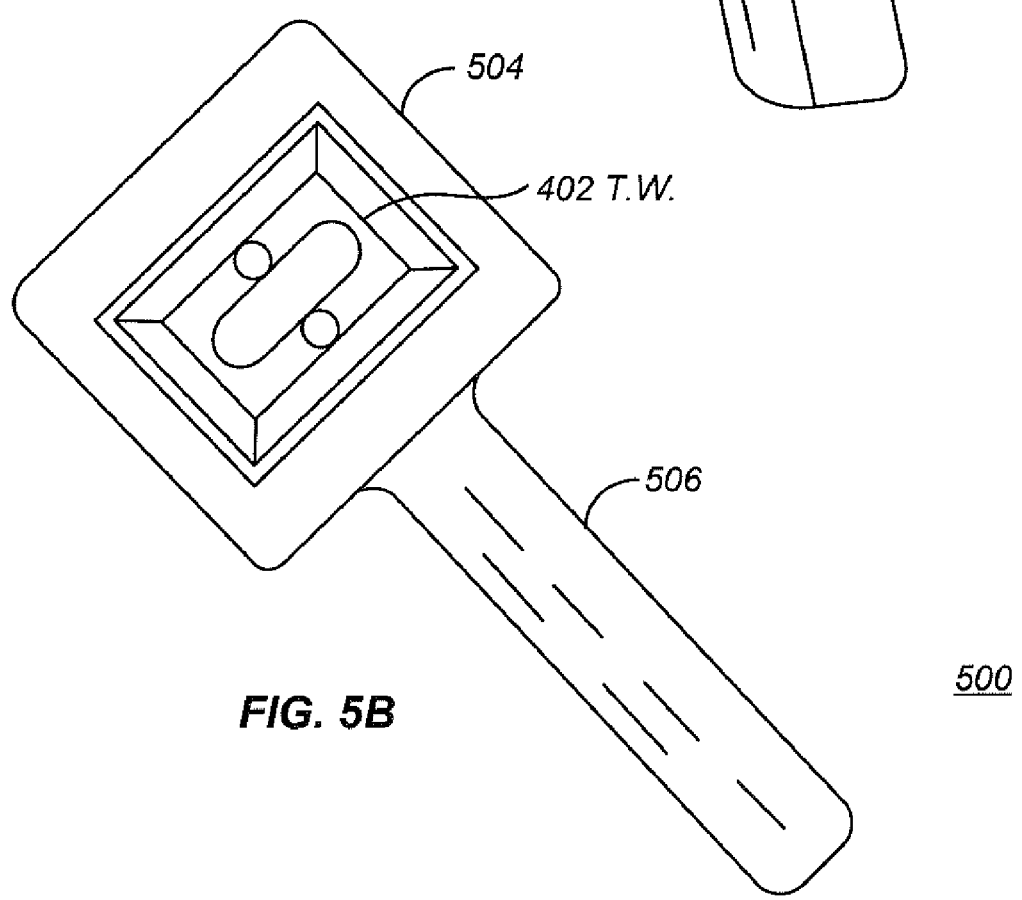
FIG. 5B is a representative view of the treatment window in the front end of the handpiece shown in FIG. 5A.

FIG. 5A is a representative isometric view of another preferred embodiment of the handpiece 500 of the present invention for treating skin disorders according to the method of the present invention. FIG. 5B is a representative view of the treatment window 402 in the front end 504 of the handpiece 500 shown in FIG. 5A. In this preferred embodiment, the handpiece 500 comprises a curved or bent, pistol-shaped, handle portion 506 coupled to the front end 504 that has a hood 408 which protrudes outwardly from a flashlamp in defining a treatment site.

The treatment window 402 is only about 3 cm×4 cm, or about 12 cm². it will be understood that the shape of the treatment window 402 can be rectangular or square, round or other operative or ornamental shape.

Figure 6A:
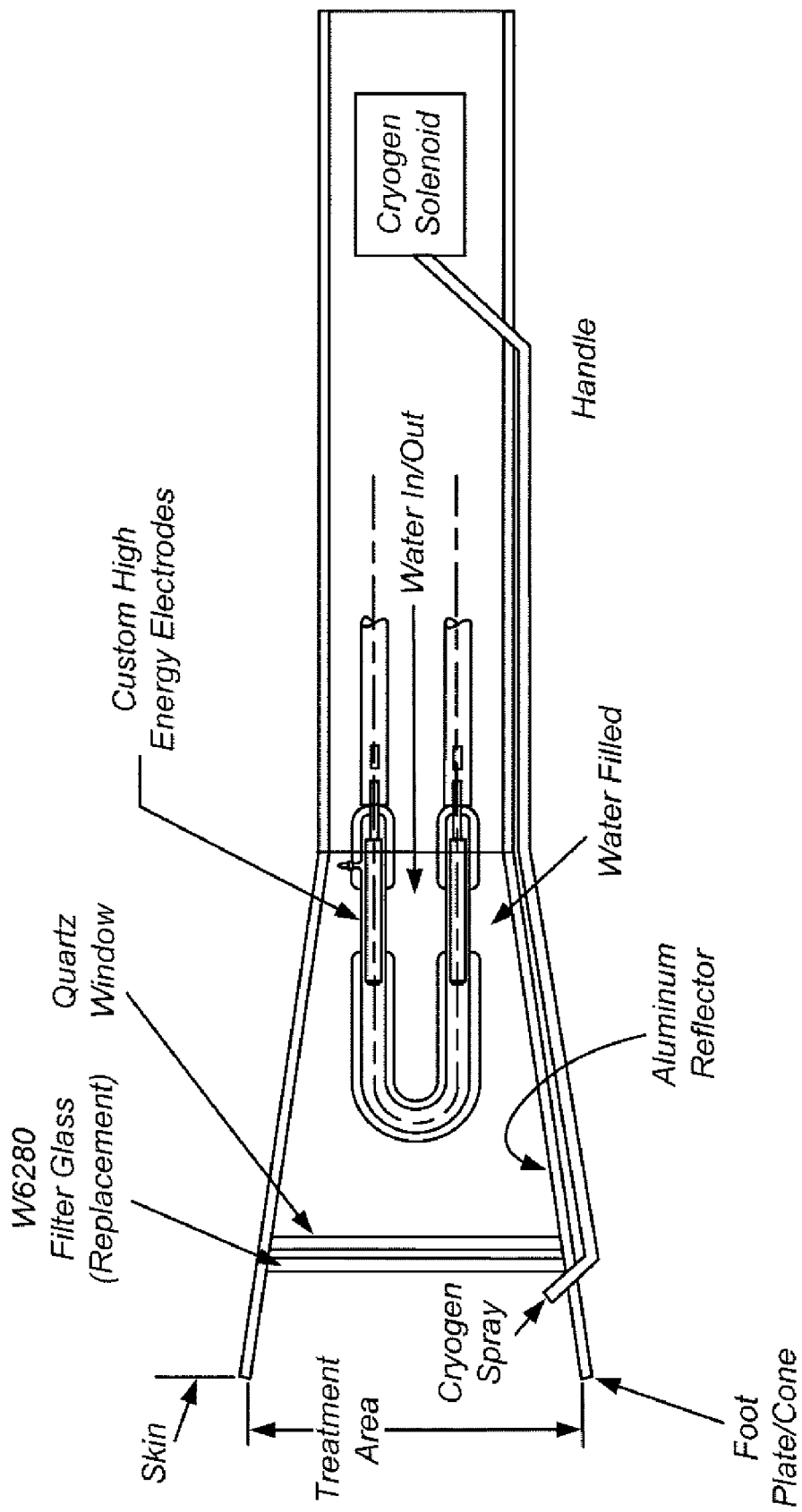
FIG. 6A is a representative isometric view of yet another preferred embodiment of the handpiece of the present invention for treating skin disorders according to the method of the present invention.
Figure 6B:
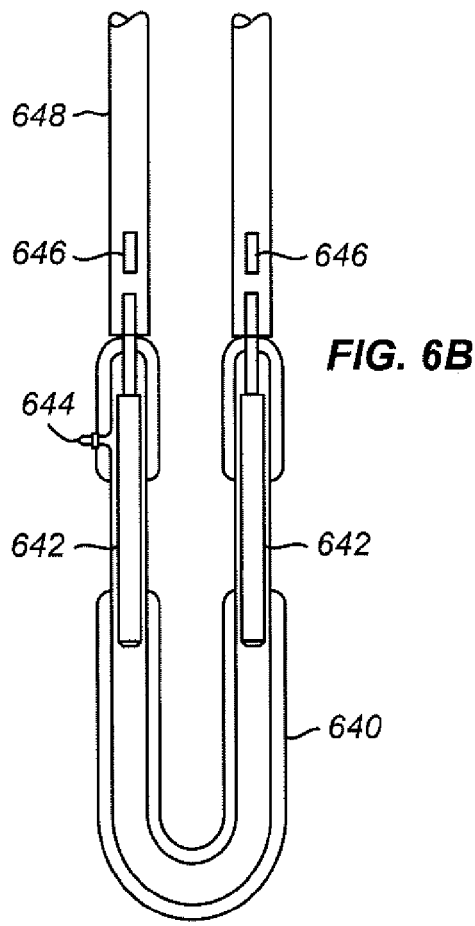
FIG. 6B is a representative view of the flashlamp portion of the handpiece shown in FIG. 6A.

FIG. 6A is a representative isometric view of yet another preferred embodiment of the handpiece 600 of the present invention for treating skin disorders according to the method of the present invention. FIG. 6B is a representative view of the flashlamp portion 602 of the handpiece 600 shown in FIG. 6A. It will be understood from the foregoing that the embodiments shown in FIGS. 4A–5B as well as others may be constructed with as follows.

The handpiece 600 has a handle portion 606 which contains various connectors and other systems. A treatment window 604 at the front end 608 comprises a quartz glass window 610. The flashlamp 602 may be a gas discharge device filled with xenon or krypton gas. It may be linear, helical or U shaped. The flashlamp 602 will be capable of operation in a near black body mode. Energy emitted by the flashlamp 602 will be concentrated. The flashlamp 602 will be cooled by water in one embodiment and by airflow in another. Filters 612 may be used to control the energy spectrum, for example BG1 filter glass for UVB operation. Other filters 612 may be used to operate in different portions of the spectrum.

The housing 620 of the handpiece 600 also has a cooling fluid inlet 622 and chamber area 624 for circulation of cooling fluid. this chamber is defined, in a preferred embodiment, by an aluminum or other reflective surface 626. Optionally, a solenoid or other control valve means 630 allows cooling fluid or other coolant to flow to a treatment site 632 from the distal tip 636 of a delivery tube 634 or other directional focusing means as, when and how desired.

In one preferred embodiment of the present invention, the looped flashlamp 602 may be dual and wired in series. This allows greater lifetime for the lamp 602 while maintaining a compact source area. The looped design of the flashlamp 602 allows a much more compact reflector 626 design and simplifies the task of holing up, sealing and configuring electrical connections and circulating cooling water around the lamp 602.

The flashlamp tube 602 comprises a unshaped, hollow glass tubular section 640 with hollow, tubular electrodes 642 extending from both sides. On one electrode 642, a fill port 644 provides a convenient access port for filling the flashlamp 602 with the desired gas, such as xenon or krypton gas. Electrical leads 646 provide a source of power to the electrodes 642. the electrical leads 646 can be exposed but can also be jacketed or cooled 648.

Figure 6C:
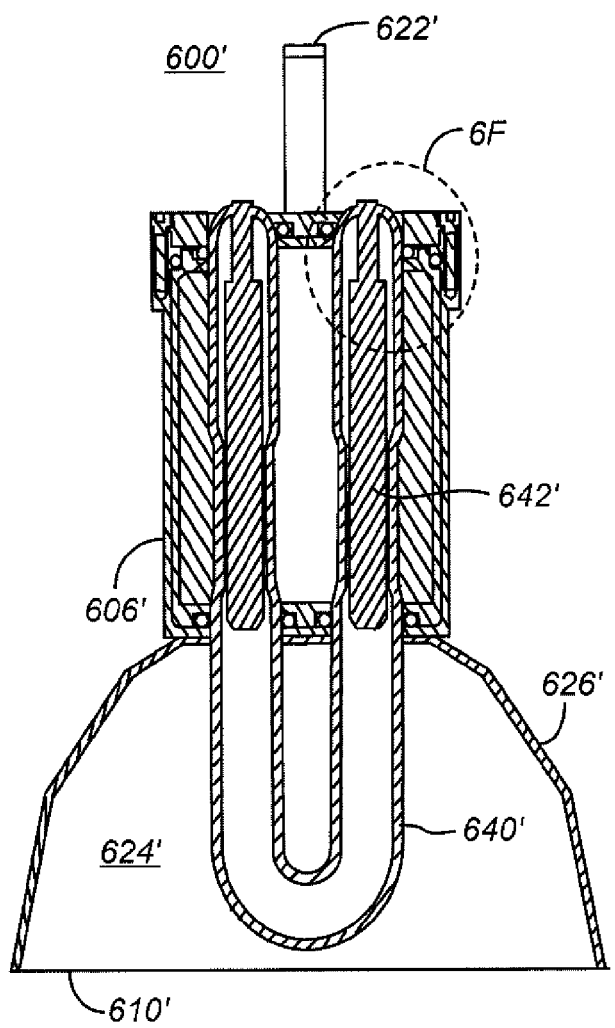
FIG. 6C is a representative front section view of yet another preferred embodiment of the handpiece of the present invention for treating skin disorders according to the method of the present invention.
Figure 6D:
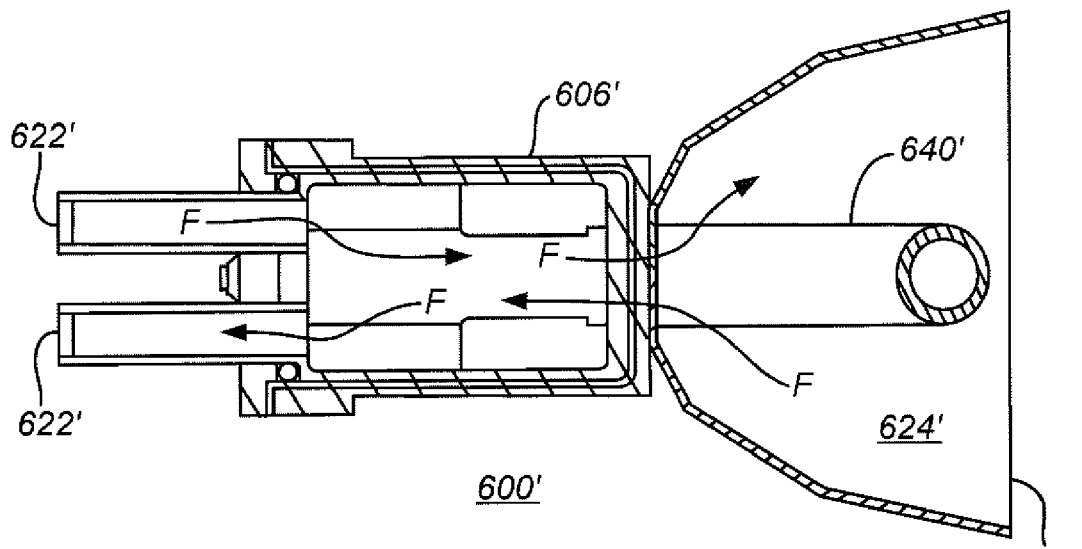
FIG. 6D is a representative side section view of the handpiece of the present invention such as shown in FIG. 6C.
Figure 6E:
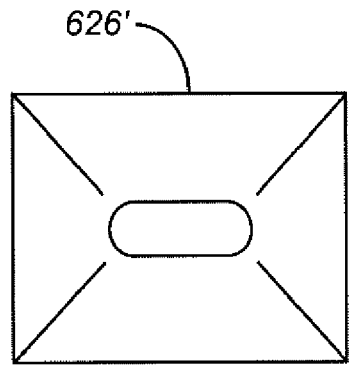
FIG. 6E is a representative lower view of the reflector of the present invention such as shown in FIG. 6C.
Figure 6F:
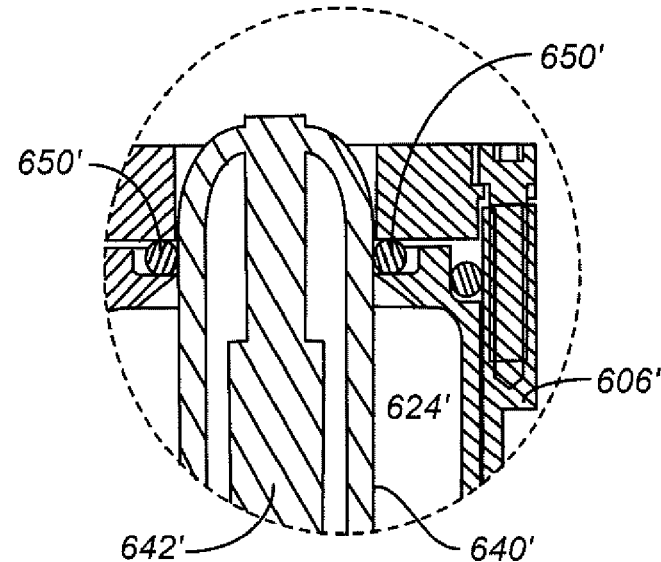
FIG. 6F is a representative detail view showing a portion of the handpiece of the present invention such as shown in FIG. 6C.

FIG. 6C is a representative front section view of yet another preferred embodiment of the handpiece 600' of the present invention for treating skin disorders according to the method of the present invention. FIG. 6D is a representative side section view of the handpiece 600' of the present invention such as shown in FIG. 6C. FIG. 6E is a representative lower view of the eliptical reflector portion 626' of the present invention such as shown in FIG. 6C. FIG. 6F is a representative detail view showing a portion of the handpiece 600' of the present invention such as shown in FIG. 6C.

As described above, the flashlamp 602 comprises a unshaped glass, tubular section 640' filled with the desired gas. Electrodes 642' are coupled to high power electrical leads. Cooling fluid flows through inlet and outlet 622'. Front glass window section 610' and handle portion 606' define a cooling fluid chamber 624' and fluid seals or sealing membranes or glands 650' keep the cooling fluid separated and isolated from the electrodes 642' and electrical leads. Fluid flow is indicated by directional arrows F.

As described above, the reflector 626' can be any suitable or appropriate and operative shape and material of construction, including circular, elliptical, faceted, aluminum, stainless steel, gold, silver, and can comprise a doped material including tin or titanium doped quartz for blocking the deep UV rays, etc. A dielectric filter is also highly valuable and increases the utility when used in conjunction with the handpiece 600' of the present invention.

Figure 7A:
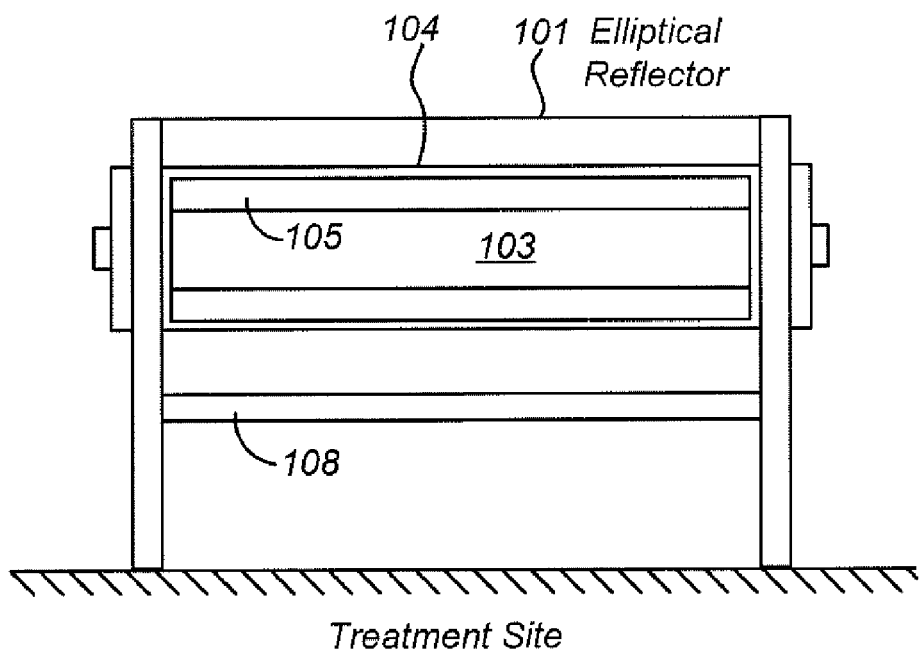
FIG. 7A is a representative side view of a preferred embodiment of a non-contact treatment apparatus of the present invention for treating skin disorders according to the method of the present invention.
Figure 7B:
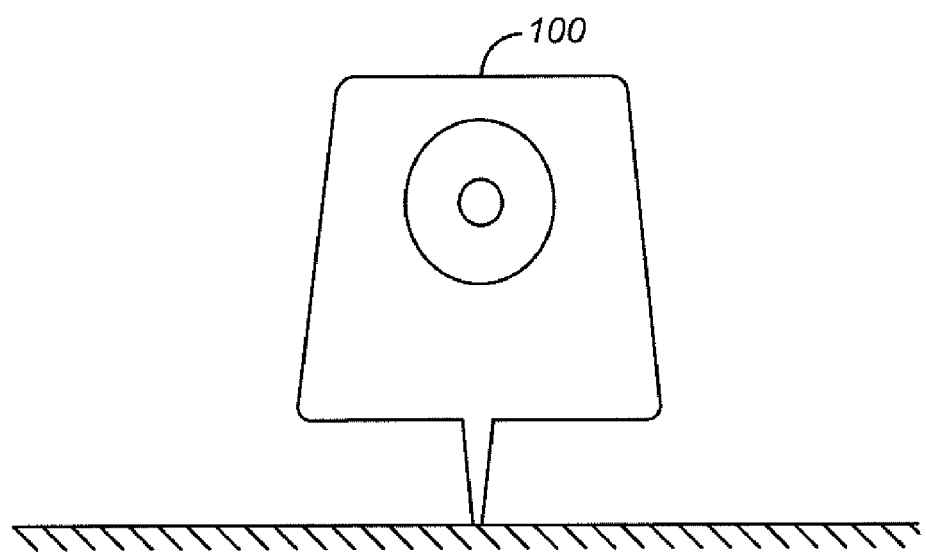
FIG. 7B is a representative side view of the treatment apparatus shown in FIG. 7A.

FIG. 7A is a representative side view of a preferred embodiment of a non-contact treatment apparatus 700 of the present invention for treating skin disorders according to the method of the present invention. FIG. 7B is a representative side view of the treatment apparatus 700 shown in FIG. 7A.

Figure 8A:
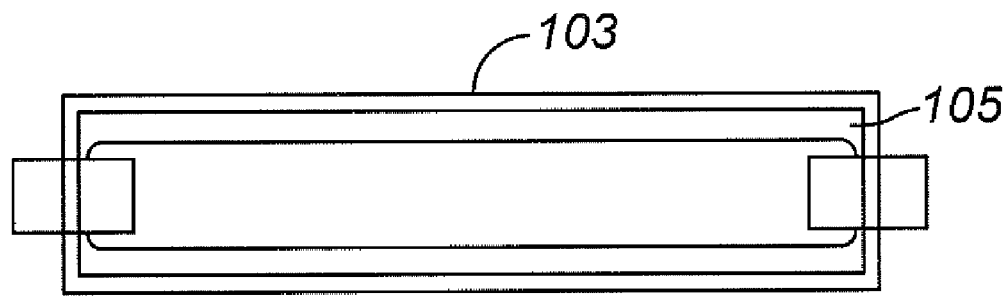
FIG. 8A is a representative side section view of a preferred embodiment of a blackbody flashlamp with filter within a water filled flow tube of the present invention for treating skin disorders according to the method of the present invention.
Figure 8B:
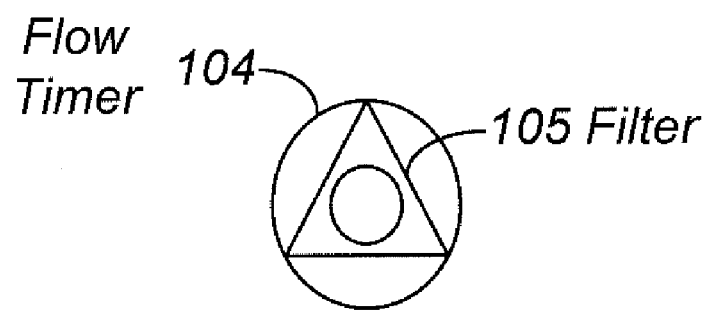
FIG. 8B is a representative end section view of the flashlamp with filter within a water filled flow tube shown in FIG. 8A.

FIG. 8A is a representative side section view of a preferred embodiment of a blackbody flashlamp 702 with filter 712 within a water filled flow tube 740 of the present invention for treating skin disorders according to the method of the present invention. FIG. 8B is a representative end section view of the flashlamp 702 with filter 712 within a water filled flow tube 740 shown in FIG. 8A.

Figure 9:
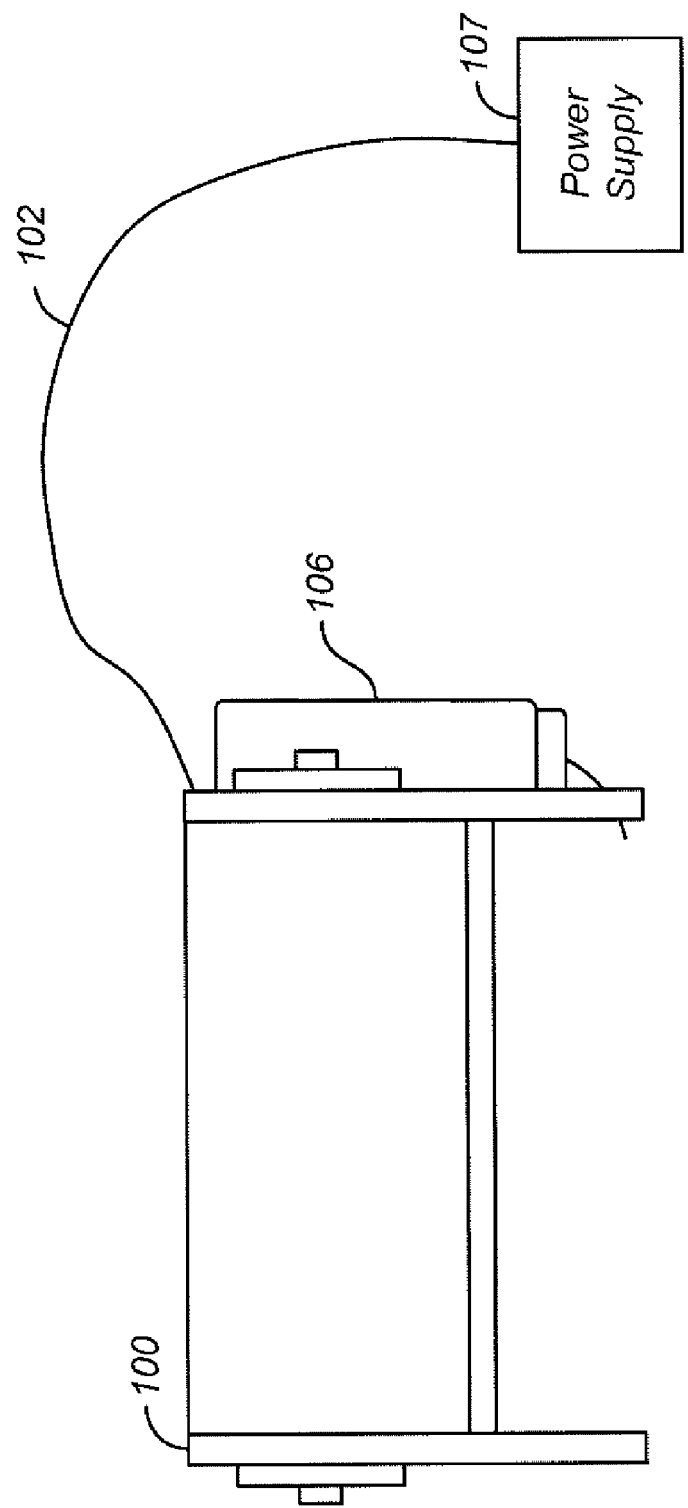
FIG. 9 is a representative schematic view of a preferred embodiment of a blackbody treatment apparatus with cooling system and remote resource and/or controller communication system of the present invention for treating skin disorders according to the method of the present invention.

The delivery system 700 consists of a housing 708 that encloses an elliptical reflector 726, a flashlamp 702, flow tube 740, filters 712 and cooling fluid chamber 724 for the flashlamp 702 and filters 712. Another embodiment (as shown in FIG. 9) includes cooling system for the treatment site 632.

The housing 708 may have a handle portion (not shown) to facilitate the directed delivery of therapeutic light to the treatment site 632. In another embodiment, the housing 708 may be attached to a mechanical articulating arm (not shown) so that the operator doesn't need to support the entire weight of the delivery system 700 unassisted. Attached to the housing 708 will be an umbilical 750 or other means for communicating containing high voltage wires and cooling tubes (not shown). In another embodiment, the housing 708 may accommodate a means of cooling the treatment site 632 with $CO^2$ gas, cryogen air/water or other cooling agents. The reservoir 730 or other container holding the cooling agent may be mounted directly onto the housing 708 or it may be remote. In the remote configuration, the cooling agent may be delivered via a tube in the umbilical 750 or by another means. The cooling agent container 730 may be disposable or refillable. A delivery tube 734 or other directional providing means provides a way to control the angle or direction of flow of the cooling agent directly to the skin or other target material. The umbilical 750, as described above, comprises optionally and as examples, an exterior thermoplastic or rubber casing, a protective and shielding braided layer or jacket having a dimension of about 0.525 mils diameter or more or less, individually insulated high and low power electrical wires for operating and control power having gauges between about 14 AWG and 22 AWG or more or less and having different color and material insulating layers including rubber or silicone, tubes made of HDPE or PTFE or other operative material having about ¼" to about ⅛" OD or more or less to about ⅛" to about ¹⁄₁₆" ID or more or less for cooling agents and cooling fluids for the lamp and the treatment area. The elliptical reflector 726 will be designed to focus the maximum amount of energy onto the treatment site 632. The reflective surface 728 may be faceted and/or polished, and made of aluminum, gold, silver or other formed or other reflective materials. The surface 728 may also and optionally be protected or unprotected.

The flowtube 740 will enclose the flashlamp 702 and and filters 712. Water or other temperature regulating material will flow through the flowtube 740 to cool both the flashlamp 702 and the filters 712 while allowing the treatment energy to exit through the flowtube 740. The flowtube 740 may be made of titanium doped quartz or other material that is transparent at the treatment wavelengths. In another embodiment, the flowtube 740 may be coated with a reflective coating, which will act as a filter to control the operation of the device within the chosen portion of the spectrum.

The filters 712 may be absorbing filter glass to filter out unwanted wavelengths of energy. They may be arranged around the flashlamp 702 in such a manner that no unfiltered energy can escape. They may be arranged in such a manner that they will be cooled by the flashlamp 702 coolant. In another embodiment, the filters 712 may be cooled by flowing air.

The filters 712 may be titanium doped quartz or another glasslike substance coated with a reflective coating to remove unwanted wavelengths. The flow tube 740 may be coated in a similar manner so that it is used as the filter 712.

An optional or additional filter 712 may be placed between the flashlamp 702 and the treatment site 632 to filter out visible and infrared radiation. This filter 712 may be quartz or other material coated as a "hot mirror". In another embodiment, this coating may be applied to the flowtube 740. The filters 712 can be changed by snapping their holders on and off. An electrical connection 750 to the handpiece 700 may be used to allow the power supply console 752 to identify and calibrate the user display.

Figure 3A:
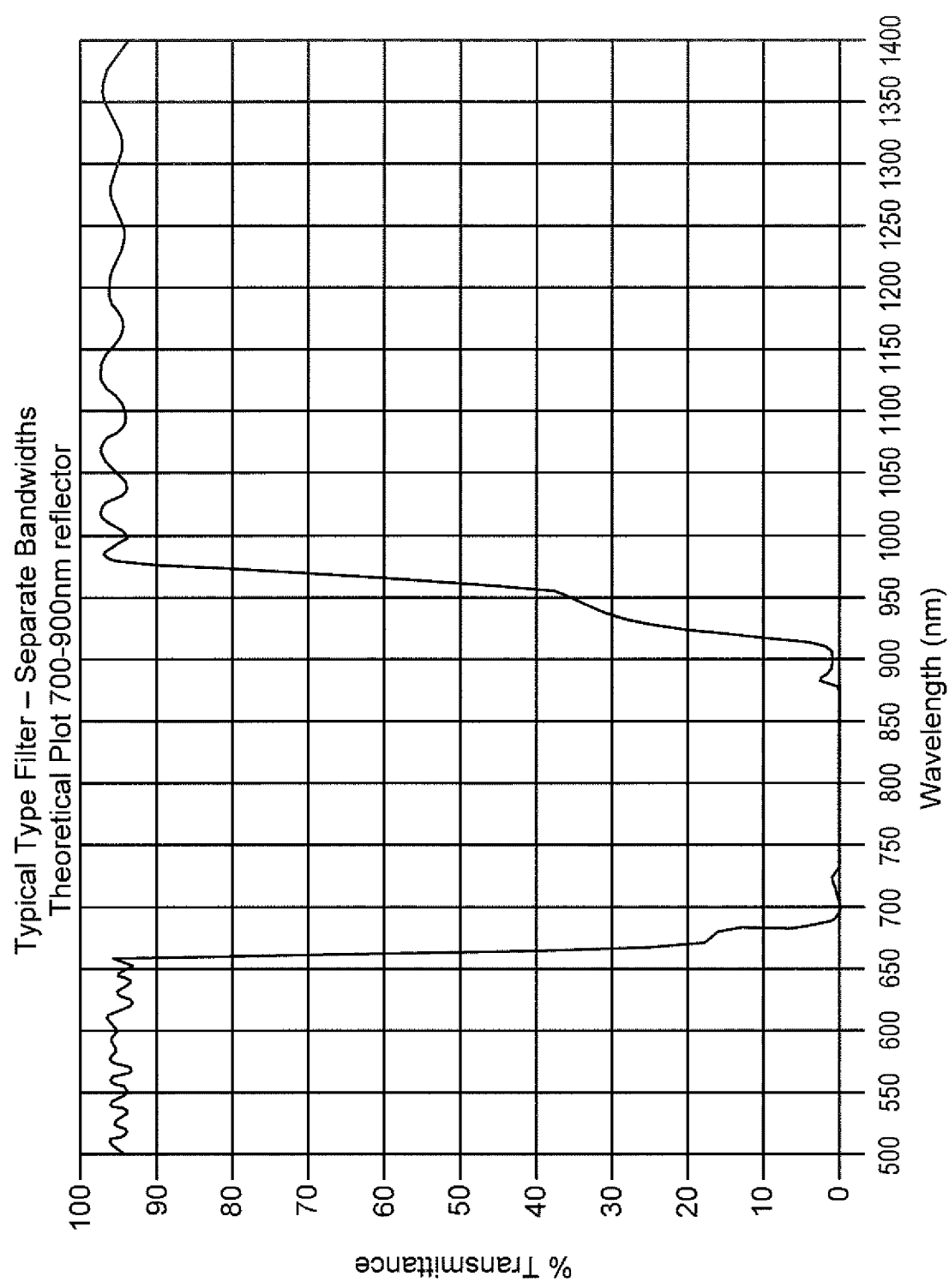
FIG. 3A illustrates the thoretical plot of transmittance of light through a typical 700–900 nm filter such as used in the apparatus and method of the present invention.
Figure 3B:
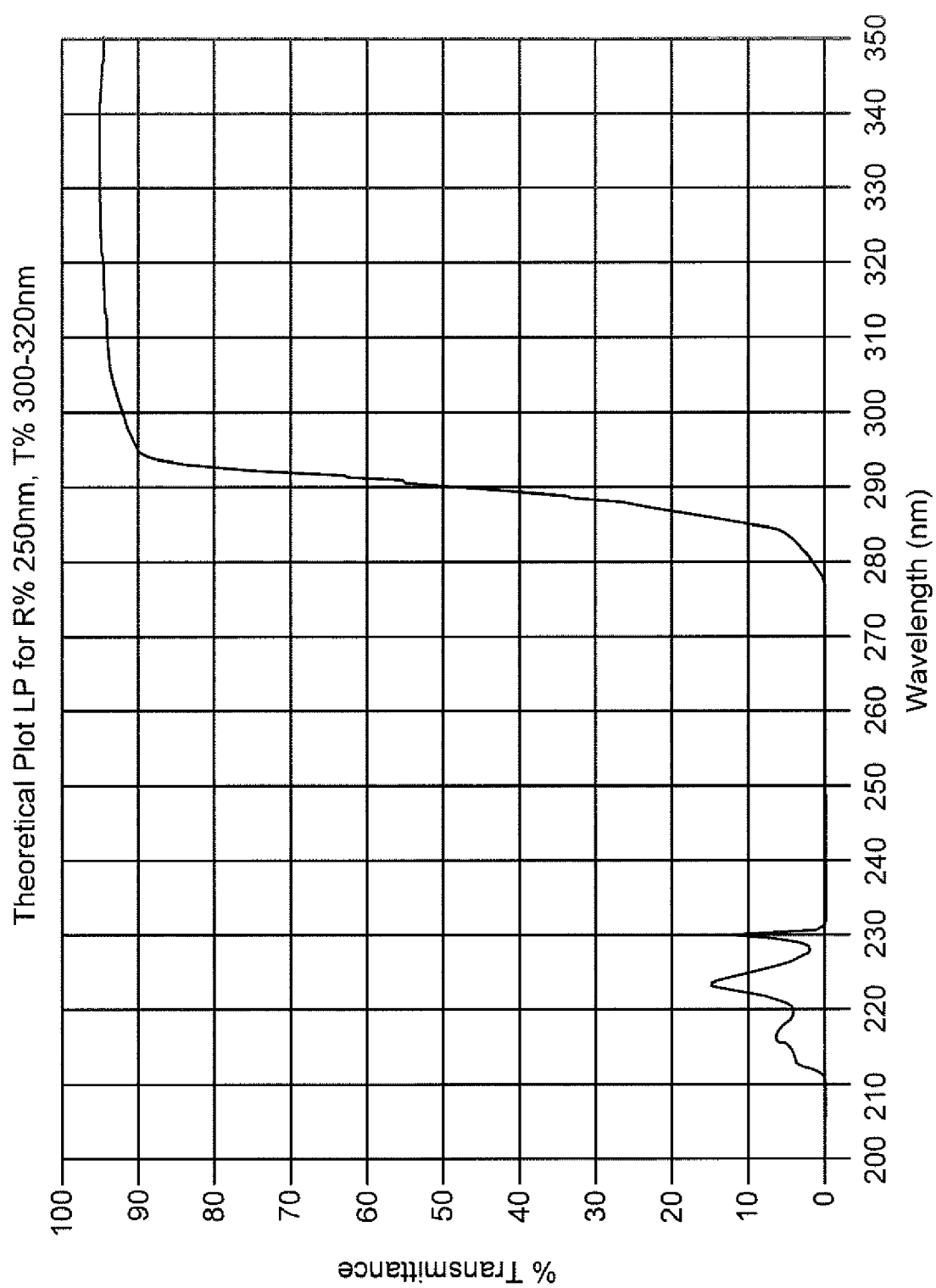
FIG. 3B illustrates the thoretical plot of transmittance of light through a typical LP for R % 250 nm, T % 300–320 nm such as used in the apparatus and method of the present invention.

FIG. 3A illustrates the theoretical plot of transmittance of light through a typical 700–900 nm filter such as used in the apparatus and method of the present invention. FIG. 3B illustrates the thoretical plot of transmittance of light through a typical LP for R % 250 nm, T % 300–320 nm such as used in the apparatus and method of the present invention.

FIG. 9 is a representative schematic view of a preferred embodiment of a blackbody treatment apparatus 700 with cooling system 730 and remote resource and/or controller communication system 752 of the present invention for treating skin disorders according to the method of the present invention.

Cooling for the flashlamp 702 and filters 712 may be achieved by flowing water over them within the flowtube. The water will then be cooled by a water to air heat exchanger enclosed (not shown) with the power supply 752. In another embodiment, the flashlamp 702 and filters 712 will be cooled by airflow provided by a fan (not shown). Cooling to the treatment site 632 may use $CO_2$ gas, Cryogen, air/water or other cooling agents. These cooling agents may be delivered to the treatment site 632 by activating a solenoid 630 or other switch. The container 730 containing the cooling agent may be mounted on the delivery system 700. The container 730 may be disposable or refillable. In another embodiment, the container may also be remote (and therefore not shown) to the delivery system and delivered to the treatment site 632 via a tube 734 or other means. In the remote embodiment, the container (not shown) may be disposable or refillable.

Apertures at the tip 636 of the delivery tube 634 or 734 of varying sizes may be used to protect the healthy skin from exposure to the treatment energy while allowing the sufficient and adequate exposure to affected skin.

Figure 10A:
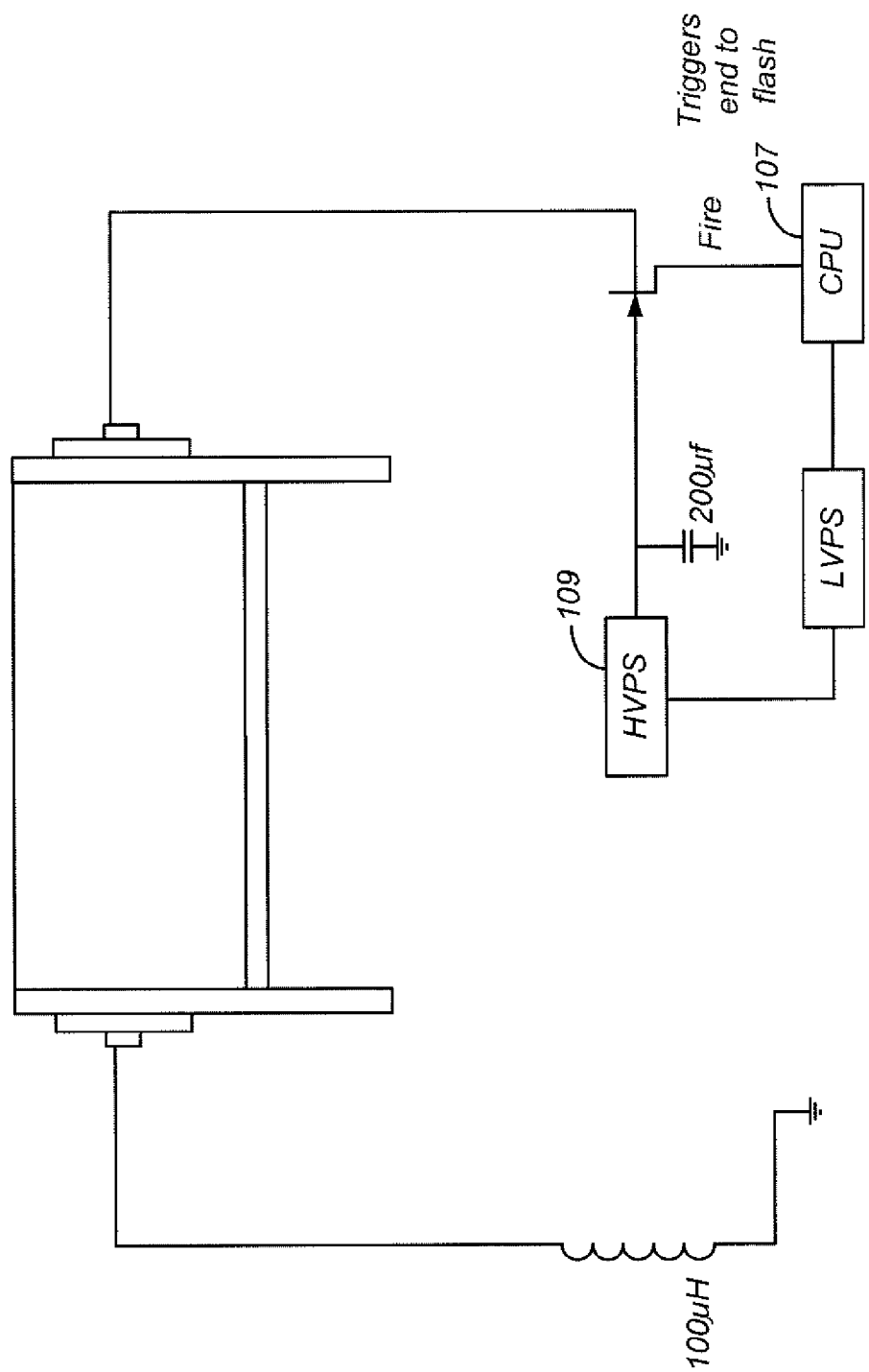
FIG. 10A is a representative electronic circuit diagram of a preferred embodiment of a blackbody treatment apparatus of the present invention for treating skin disorders according to the method of the present invention.
Figure 10B:
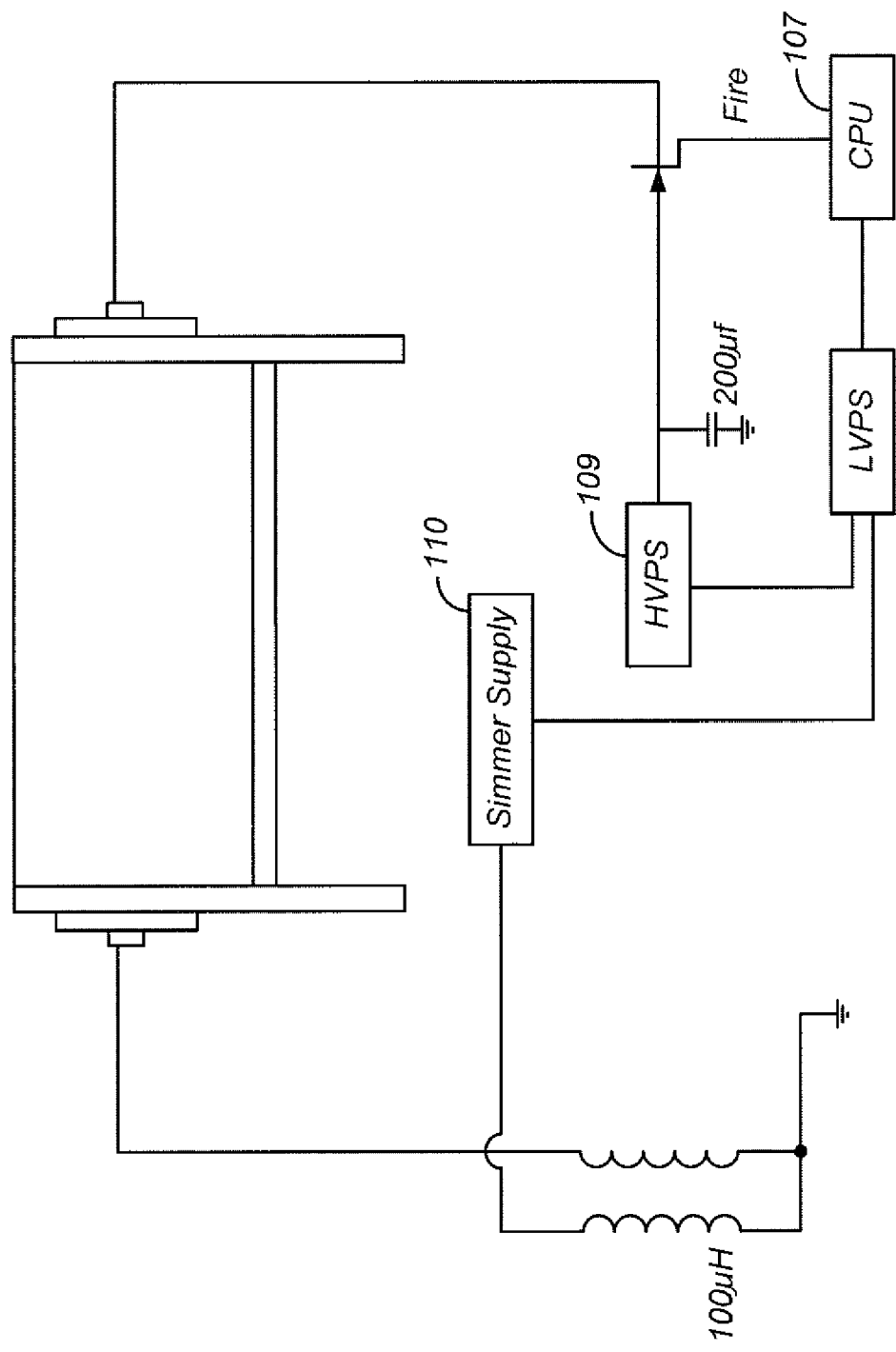
FIG. 10B is another representative electronic circuit diagram of a preferred embodiment of a blackbody treatment apparatus of the present invention for treating skin disorders according to the method of the present invention.

FIG. 10A is a representative electronic circuit diagram 1000 of a preferred embodiment of a blackbody treatment apparatus 1002 of the present invention for treating skin disorders according to the method of the present invention. FIG. 10B is another representative electronic circuit diagram 1000' of a preferred embodiment of a blackbody treatment apparatus 1002 of the present invention for treating skin disorders according to the method of the present invention.

The circuit 1000 comprises a high voltage source power supply 1004 and a low voltage power supply (LVPS) 1005. A pulse forming network (PFN or switchable PFN) 1010 regulates a water to air heat exchanger and a controller 1016. The PFN 1010 may be comprised of a single inductor 1012 and multiple storage capacitors 1014. With this configuration, bursts containing multiple pulses can be produced by trigger or switch 1018. The burst width may be adjusted by varying the time between pulses and by adjusting the number of pulses per burst. The output energy can be adjusted by varying the high voltage.

The power supply 1020 may be microprocessor controlled 1016 and provide high voltage pulses to the flashlamp 702, cooling for the lamp 702 and filters 712 and control for treatment site 632 cooling. The power supply 1020 may contain safety monitoring and feedback devices (not shown). The temperature of the treatment site 632 may be monitored and data utilized therefrom in a selected control scheme or protocol. In a preferred embodiment of the system and method of the present invention 1000' as shown in FIG. 10B, the flashlamp 702 may be simmered 1250. In another, as shown in FIG. 10A, the circuit 1000 may be unsimmered. The simmer circuit is a form of pre-excitation of the power circuit. It will be understood that the simmer circuit comprises a capacitor and resistor with switch. In a preferred embodiment, the simmer current can be monitored, and in the event of simmer circuit failure, the power to the system shuts off and the capacitor releases any stored charge through a resistor to completely prevent any power from being transmitted as far as the handpiece. Thus, in the DC mode, a string of low voltage pulses maintain the gas at an elevated temperature and energy level, and subsequent application of a high voltage, such as about 1500 volts or more or less, causes a self-sustaining ionization of the gas used in the filled flashlamp. Flashlamp pressure can be about 450 Torr or more or less.

Additional pulsed blackbody, deep-UV radiators and water purifications systems are described in U.S. Pat. Nos. 6,117,335 and 6,200,466, both entitled DECONTAMINATION OF WATER BY PHOTOLYTIC OXIDATION/REDUCTION UTILIZING NEAR BLACKBODY RADIATION, both of which are hereby expressly incorporated by reference in their entireties herein.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A handpiece for treatment of skin conditions, comprising:
   a hand-held housing having a light transmissive opening and a cryogen source;
   a flashlamp disposed in the housing for generating an output electromagnetic radiation through the opening onto a treatment site; and
   a treatment site cooling system including a port disposed on the housing near the opening, adapted for delivery of a cryogenic cooling fluid from the cryogen source to protect skin in the treatment site from burning caused by exposure to the electromagnetic radiation, wherein the cryogen source is contained within the housing.

2. The handpiece of claim 1 wherein the housing includes a hood which protrudes outwardly from the flashlamp, defining an area of the treatment site, and said port is positioned on the hood.

3. The handpiece of claim 1 wherein the port comprises a nozzle for spraying the cryogenic cooling fluid onto the treatment site.

4. The handpiece of claim 1 further comprising a switch for controlling the delivery of the cryogenic cooling fluid in timed relationship with the flashlamp.

5. The handpiece of claim 4 wherein the switch comprises an electrical solenoid valve.

6. The handpiece of claim 4 further comprising a delivery tube coupled to the switch for delivering the cryogenic cooling fluid to the treatment site.

7. The handpiece of claim 1 further comprising one or more filters disposed between the flashlamp and the opening for filtering electromagnetic radiation and passing desirable wavelengths to the treatment site.

8. The handpiece of claim 7 wherein the one or more filters comprise first and second regions for allowing simultaneous delivery of UV and IR electromagnetic radiation to the first region while blocking the second region that has no therapeutic effect.

9. The handpiece of claim 7 wherein the one or more filters are band pass filters with first and second regions for allowing simultaneous delivery of UV and IR electromagnetic radiation to the first region while blocking the second region that has no therapeutic effect.

10. The handpiece of claim 7 wherein the flashlamp comprises a hollow tubular section with an interior that is u-shaped or helical.

11. The handpiece of claim 10 further comprising a source of cooling fluid that is fluidly coupled to the hollow tubular section to provide a cooling fluid to the hollow tubular section of the flashlamp and the one or more filters.

12. The handpiece of claim 10 further comprising a cooling fluid chamber at least partially enclosing the hollow tubular section.

13. The handpiece of claim 12 wherein the source of cooling fluid is fluidly coupled to the cooling fluid chamber.

14. The handpiece of claim 12 further comprising a fluid inlet and a fluid outlet that are coupled to the cooling fluid chamber for cooling the flashlamp and the one or more filters.

15. The handpiece of claim 14 wherein the fluid inlet and the fluid output are both fluidly coupled to the source of cooling fluid.

16. The handpiece of claim 1 further comprising a controller for driving the flashlamp at a predetermined pulse rate to produce electromagnetic radiation directed at the treatment site in the opening in coordination with the delivery of cryogenic cooling fluid to the treatment site.

17. The handpiece of claim 16 wherein the controller varies the predetermined pulse rate at which electromagnetic radiation is delivered to the treatment site in the treatment window.

18. The handpiece of claim 16 wherein the controller drives a predetermined energy intensity level to the treatment site in the opening.

19. The handpiece of claim 18 wherein the controller varies the predetermined energy intensity to the treatment site in the opening.

20. The handpiece of claim 16 wherein the controller drives the flashlamp to produce near black body electromagnetic radiation.

* * * * *